(12) United States Patent
Asafusa et al.

(10) Patent No.: US 9,089,873 B2
(45) Date of Patent: Jul. 28, 2015

(54) ULTRASONIC PROBE AND ULTRASONIC DIAGNOSTIC APPARATUS

(75) Inventors: Katsunori Asafusa, Tokyo (JP); Makoto Fukada, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 652 days.

(21) Appl. No.: 12/668,478

(22) PCT Filed: Jul. 1, 2008

(86) PCT No.: PCT/JP2008/061874
§ 371 (c)(1),
(2), (4) Date: Jan. 11, 2010

(87) PCT Pub. No.: WO2009/008282
PCT Pub. Date: Jan. 15, 2009

(65) Prior Publication Data
US 2010/0198070 A1    Aug. 5, 2010

(30) Foreign Application Priority Data

Jul. 11, 2007   (JP) ................................. 2007-181570

(51) Int. Cl.
*A61B 8/14*    (2006.01)
*A61B 8/00*    (2006.01)
*B06B 1/02*    (2006.01)

(52) U.S. Cl.
CPC ............. *B06B 1/0292* (2013.01); *A61B 8/4444* (2013.01); *A61B 8/4494* (2013.01)

(58) Field of Classification Search
CPC .. A61B 8/4444; A61B 8/4494; A61B 8/4484; A61B 8/00; B06B 1/0292; B06B 2201/51
USPC ......................................... 600/407, 437, 459
See application file for complete search history.

(56) References Cited

U.S. PATENT DOCUMENTS

| | | | |
|---|---|---|---|
| 6,605,043 B1 | 8/2003 | Dreschel et al. | |
| 6,831,394 B2 * | 12/2004 | Baumgartner et al. | 310/334 |
| 7,087,023 B2 * | 8/2006 | Daft et al. | 600/459 |
| 2005/0096546 A1 * | 5/2005 | Hazard et al. | 600/447 |
| 2008/0064959 A1 * | 3/2008 | Kanda et al. | 600/459 |
| 2008/0283945 A1 * | 11/2008 | Kobayashi et al. | 257/416 |

FOREIGN PATENT DOCUMENTS

WO    WO 2006/041058 A1    4/2006

* cited by examiner

*Primary Examiner* — Katherine Fernandez
(74) *Attorney, Agent, or Firm* — Jones Robb PLLC

(57) ABSTRACT

Provided are an ultrasonic probe and an ultrasonic diagnostic apparatus, which reduce parasitic impedances which occurs in upper electrodes and lower electrodes, thereby reducing cross talk.
The ultrasonic probe comprises a cMUT chip (20) having a plurality of transducer elements, an acoustic lens (26) on the ultrasonic wave irradiation side of the cMUT chip (20), a backing layer (22) on the back of the cMUT chip (20), and wires connected with the cMUT chip (20).
This cMUT chip (20) includes a plurality of upper electrodes (46) and a plurality of lower electrodes (48), and these lower electrodes (48) are connected at two or more portions with wires.

9 Claims, 10 Drawing Sheets

ULTRASONIC PROBE AND ULTRASONIC DIAGNOSTIC APPARATUS

TECHNICAL FIELD

The present invention relates to an ultrasonic probe and ultrasonic diagnostic apparatus for transmitting/receiving ultrasonic waves.

BACKGROUND ART

Ultrasonic diagnostic apparatuses perform imaging of diagnostic images based on the reflected echo signals outputted from an ultrasonic probe. An ultrasonic probe converts drive signals into ultrasonic waves, and transmits the ultrasonic waves to an object to be examined. A plurality of ultrasonic transducers are disposed in the ultrasonic probe for receiving the reflected echo signals produced from the object and converting them into electrical signals.

In recent years, ultrasonic probes by cMUT have been developed wherein ultrasonic transmission/reception sensitivity, i.e. electromechanical coupling coefficient varies depending on the volume of bias voltage to be applied being overlapped with the drive signals to be provided from an ultrasonic transmission/reception unit. A cMUT is capacitive micromachined ultrasonic transducers manufactured by superconductor microfabrication process. A conventional technique for orthogonalizing an upper electrode and a lower electrode for the purpose of bias control is disclosed, for example, in Patent Document 1.

Patent Document 1: U.S. Pat. No. 6,605,043

DISCLOSURE OF THE INVENTION

Problems to be Solved

In power current of ultrasonic transmission/reception signals, return current flows into a lower electrode from an upper electrode via a cMUT cell. However, the fact that only one side of the upper electrode and lower electrode are pulled out in the above-described Patent Document 1 allows the occurrence of parasitic impedance such as lead inductance or loss resistance.

Thus in the case that a current flows into a common lower electrode from a plurality of upper electrodes via cMUT cells, impedance of the lower electrode fluctuates due to the influence of parasitic impedance such as lead inductance or loss resistance, thereby generating cross talk in ultrasonic transmission/reception signals. Especially, greater cross talk is generated when there is bias of lead inductance or loss resistance in the terminal pulled out from the lower electrode. The same phenomenon can also be generated in the upper electrode.

Given this factor, the objective of the present invention is, in ultrasonic probes and ultrasonic diagnostic apparatuses using cMUT, to reduce parasitic impedance generated in the upper electrode and lower electrode so as to reduce cross talk.

Means to Solve the Problem

In order to achieve the above-mentioned objective, the ultrasonic probe of the present invention comprises:
 a cMUT chip having a plurality of transducer elements;
 an acoustic lens on the ultrasonic waves irradiation side of the cMUT chip;
 a backing layer on the back surface of the cMUT chip; and
 a wiring to be connected to the cMUT chip, wherein:
 the cMUT chip has a plurality of upper electrodes and a plurality of lower electrodes; and
 the lower electrodes are connected to a wiring at two or more places. Also, the one or more wirings are equipotential.

The cross-section area which is orthogonal to the long-axis direction of the lower electrode is set so that the spacing between the upper electrode and the lower electrode becomes greater than a predetermined interval. For example, the interval between the upper electrode and the lower electrode is more than 250 nm.

Also, both ends of the lower electrode are protruded from the arranged position of the transducer elements. For example, the width of protrusion is 200 μm~1.5 mm.

Further, the end terminals of the plurality of upper electrodes are connected to the wiring indifferent directions between the adjacent upper electrodes.

Effect of the Invention

In ultrasonic probes and ultrasonic diagnostic apparatuses using cMUT, the present invention is capable of reducing cross talk by reducing parasitic impedance generated in an upper electrode or lower electrode.

BRIEF DESCRIPTION OF THE DIAGRAMS

DESCRIPTION OF REFERENCE NUMERALS

2: ultrasonic probe, 4: transmission means, 6: bias means, 8: reception means, 10: phasing adding means, 12: image processing means, 14: display means, 16: control means, 18: operation means, 20a~20m: transducer, 22: backing layer, 26: acoustic lens, 28: transducer element, 40: basal plate, 46: upper electrode, 48: lower electrode, 76: conducting layer

BEST MODE FOR CARRYING OUT THE INVENTION

Figure 1:
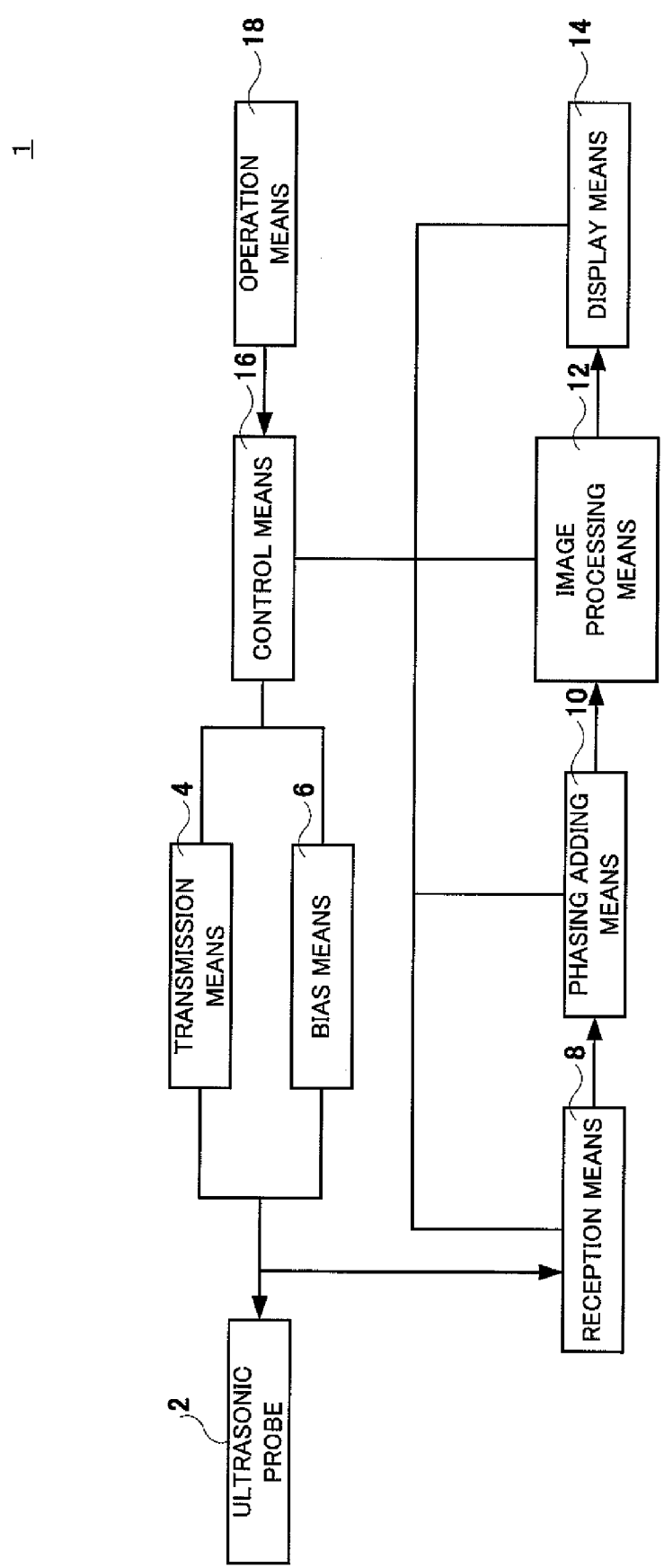
FIG. 1 shows a general configuration of the present invention.

The ultrasonic probe 2 and ultrasonic diagnostic apparatus 1 to which the present invention is applied will be described referring to the diagrams. FIG. 1 is a block diagram of the ultrasonic diagnostic apparatus related to the present invention.

As shown in FIG. 1, ultrasonic diagnostic apparatus 1 is configured by ultrasonic probe 2, transmission means 4, bias means 6, reception means 8, phasing adding means 10, image processing means 12, display means 14, control means 16 and operation means 18.

Ultrasonic probe 2 is to be applied on an object to be examined, for transmitting/receiving ultrasonic waves to/from the object. Ultrasonic probe 2 transmits ultrasonic waves to the object, and receives the reflected echo signals produced from the object.

Transmission means 4 and bias means 6 are used to provide drive signals to ultrasonic probe 2. Reception means 8 receives the reflected echo signals outputted from ultrasonic probe 2 and performs processing such as analogue digital conversion with respect to the received reflected echo signals. Phasing adding means 10 performs phasing and adding process on the received reflected echo signals. Image processing means 12 constructs diagnostic images (for example, tomographic images, blood flow images, etc.) based on the phased and added reflected echo signals. Then display means 14 displays the image processed diagnostic images on a display screen. Control means 16 is for controlling the above-described respective components. Operation means 18 is formed by a trackball or a keyboard for giving commands to control means 16.

Figure 2:
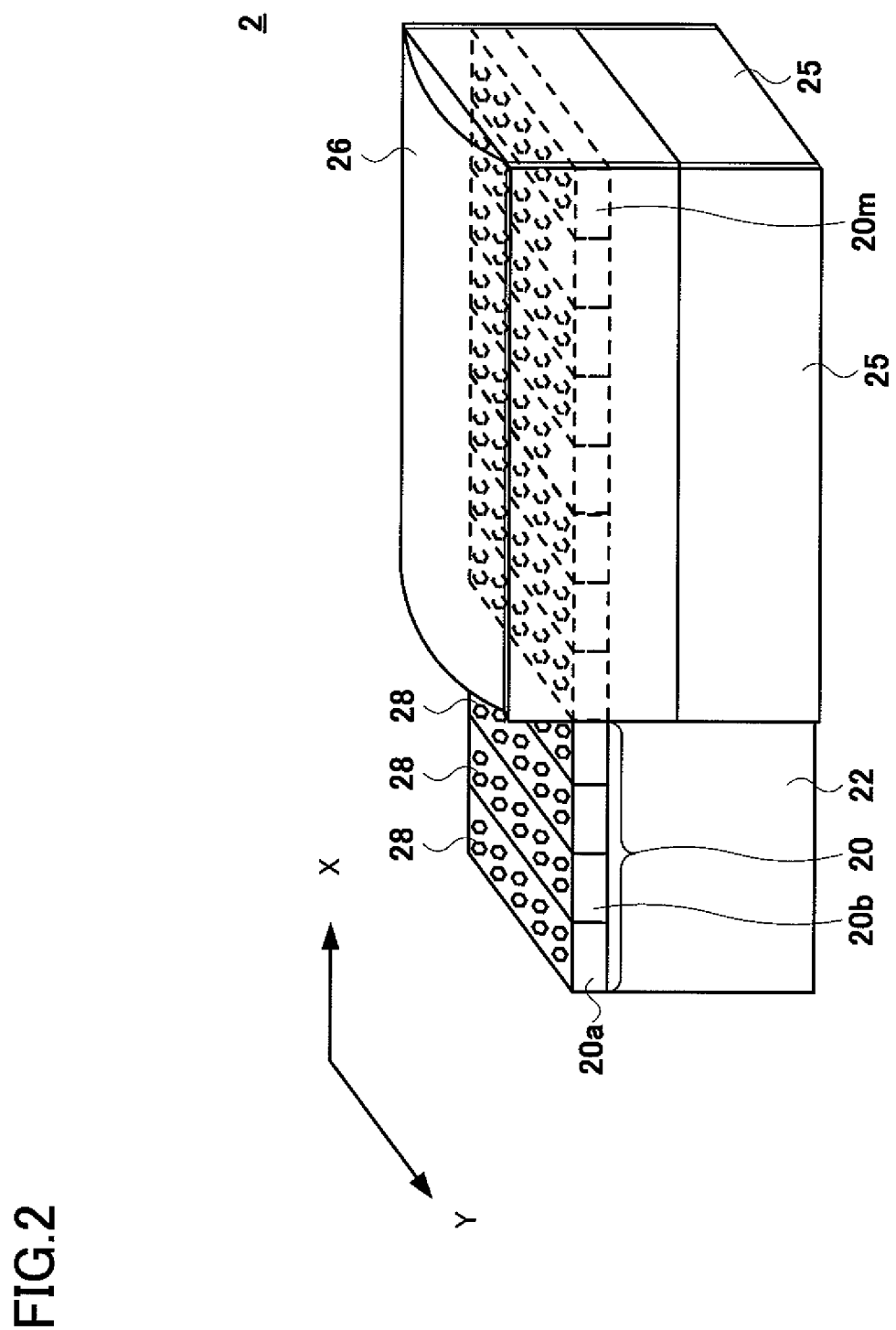
FIG. 2 illustrates the configuration of an ultrasonic probe related to the present invention.

Next, ultrasonic probe 2 will be described in detail referring to FIG. 2. FIG. 2 is an exploded perspective view of ultrasonic probe 2. Ultrasonic probe 2 is one-dimensional array type in which a plurality of transducers 20a~20m (m: whole number) are arranged into narrow strips. In this regard, however, other types such as 2-dimensional array type or convex type may also be used. Backing layer 22 is provided on the back surface side of transducers 20a~20m.

Here, a lump of transducers 20a~20m is referred to as cMUT chip 20. The detail on a CMUT is disclosed in the Non-patent Document (Capacitive Micromachined Ultrasonic Transducer: IEEE Trans. Ultrason. Ferroelect. Freq. Contr. Vol. 45, pp. 678-690, May 1998). Also, acoustic lens 26 is disposed on the ultrasonic transmitting side of cMUT chip 20. A matching layer may be inserted between acoustic lens 26 and cMUT chip 20.

Transducers 20a~20m (m: arbitrary) convert the drive signals from transmission means 4 and bias means 6 into ultrasonic waves, and transmit the ultrasonic waves to the object. Reception means 8 receives the ultrasonic waves produced from the object and converts them into electric signals to make them reflected echo signals. Backing layer 22 absorbs the transmission of the ultrasonic waves that are transmitted to the back surface side from transducers 20a~20m, and restrains the superfluous vibration. Acoustic lens 26 is for converging the ultrasonic beams transmitted from transducers 20a~20m, and the curvature is set down based on one focal distance. The matching layer for interfacing transducers 20a~20m with acoustic impedance of the object may be placed between transducers 20a~20m and the object.

Transducer 28 is an electrical/acoustic conversion element wherein electromechanical coupling coefficient, i.e. transmission/reception sensitivity varies depending on the volume of electric potential of DC bias applied by bias means 6, which converts the drive signals provided from transmission means 4 into ultrasonic waves based on the electromechanical coupling coefficient, converts the ultrasonic waves into electrical signals and receives them as the reflected echo signals.

Figure 3:
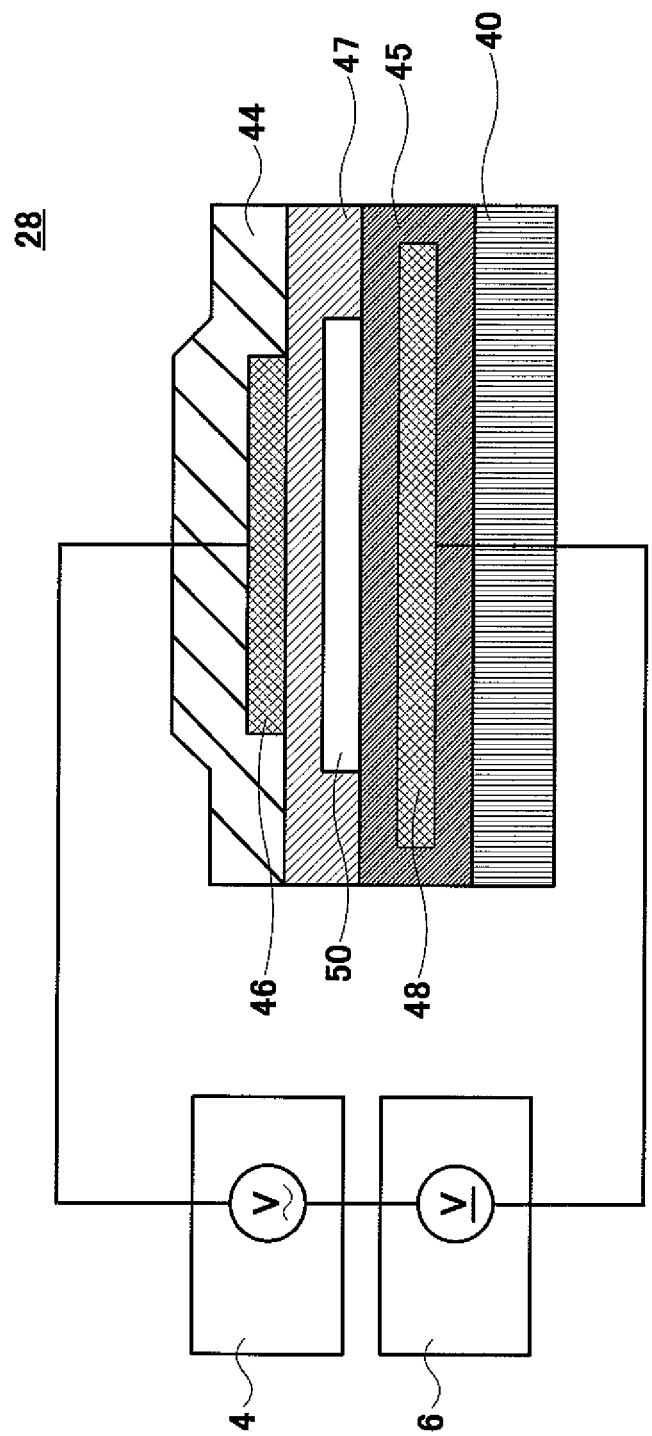
FIG. 3 is a pattern diagram showing the configuration of a transducer element related to the present invention.

FIG. 3 is a pattern diagram illustrating the configuration of transducer element 28. Transducer element 28 is formed by superconductor microfabrication process, and configured by superconductor basal plate 40, film body 44, film body 45, upper electrode 46, frame body 47, and lower electrode 48, etc. Film body 44, film body 45 and frame body 47 are formed by semiconductor compound (for example, silicon compound), and is placed on the surface of the ultrasonic waves transmission side of frame body 47. Upper electrode 46 is provided between film body 44 and frame body 47. Lower electrode 48 is provided between semiconductor base plate 40 and film body 45.

Upper electrode 46 and lower electrode 48 are connected to transmission means 4 including a power source for providing drive signals and bias means 6 for applying DC bias voltage (electric field intensity). Internal space 50 zoned by frame body 47 and film body 45 is in a condition that is either a vacuum or filled with a predetermined gas.

Here, operation of transducer element 28 will be described. First, DC bias voltage (Va) is applied to transducer element 28 via upper electrode 46 and lower electrode 48. Electric field intensity is generated by bias voltage (Va). By film body 44 being tense attributed to the generation of electric field intensity, electromechanical coupling coefficient becomes Sa. Then by provision of the drive signals from transmission means 4 to upper electrode 46, ultrasonic waves are transmitted from film body 44 based on electromechanical coupling coefficient (Sa). Also, in place of bias voltage (Va), bias voltage (Vb) is to be applied to transducer elements 28. The electromechanical coupling coefficient in this case is Sb. Then by provision of the drive signals from transmission means 4 to upper electrode 46, ultrasonic waves are transmitted from film body 44 based on electromechanical coupling coefficient (Sb). When Va<Vb, it is Sa<Sb. In the same manner, when ultrasonic waves are received, the capacitance of inner space 50 is varied due to the vibration of film body 44 being excited by the reflected echo signals produced from the object, and the electrical signals corresponding to the variation of inner space 50 is detected from upper electrode 46.

By changing the volume of bias voltage for applying to transducer element 28 so as to control the tension of film body 44, it is possible to change the acoustic pressure (for example, amplitude) of the ultrasonic waves transmitted from transducer element 28 even when the drive signal of the same amplitude is inputted.

(First Embodiment)

Figure 4:
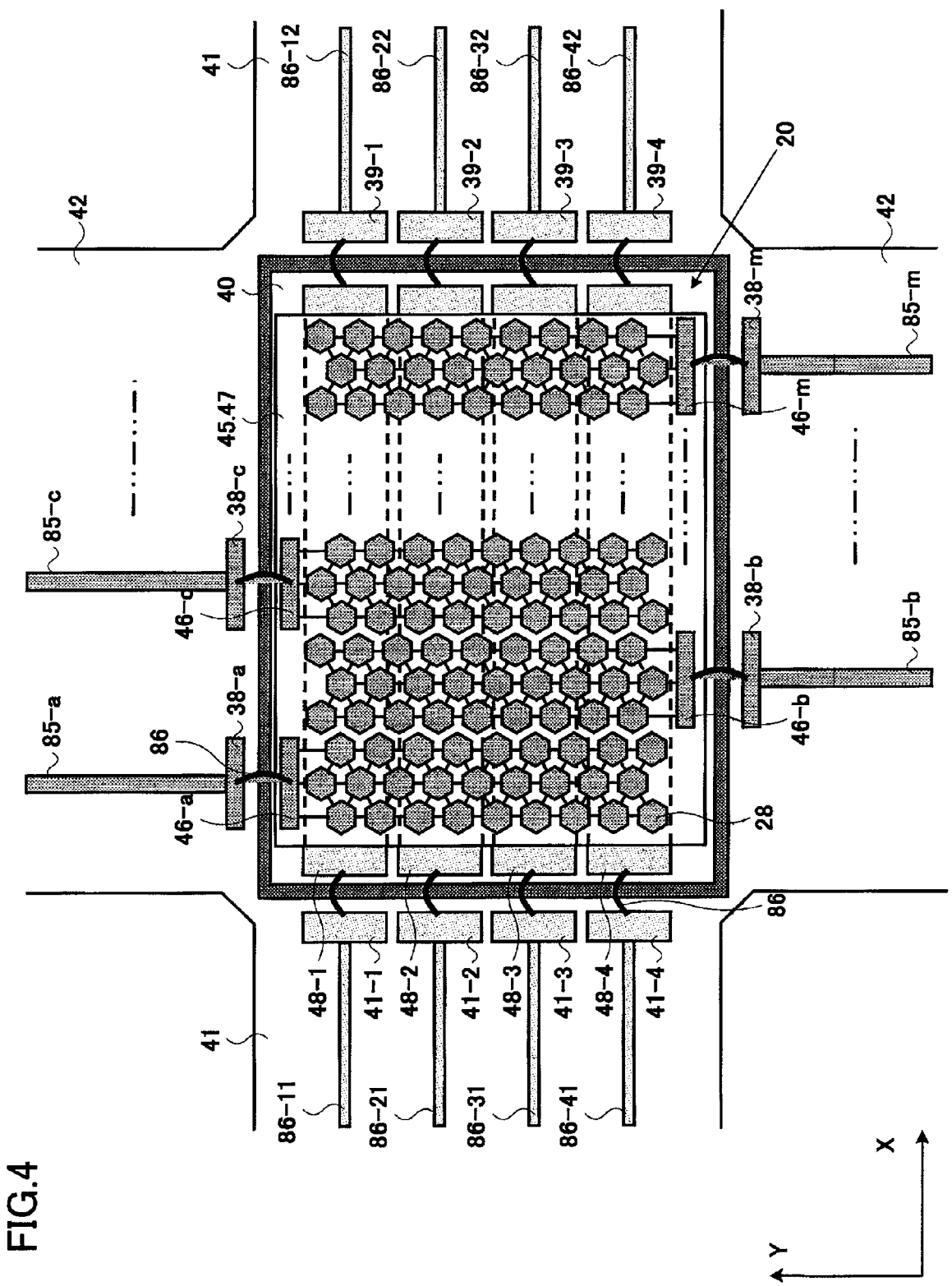
FIG. 4 illustrates first embodiment of the present invention.

Here, first embodiment and the configuration of cMUT chip 20 and the vicinity thereof will be described in detail using referring to FIG. 4. FIG. 4 is a top view of ultrasonic probe 2, and the display of film body 44 is omitted.

Superconductor basal plate 40 of cMUT chip 20 is disposed on the upper surface of backing layer 22. On the superconductor basal plate 40 of cMUT chip 20, transducer elements 28 such as upper electrode 46 and lower electrode 48 are laminated and disposed.

Also, flexible substrate 41 in the short-axis direction and flexible substrate 42 in the vertical direction are fixed on the peripheral border of the upper surface and side surface of backing layer 22. On the flexible substrate 42 in the vertical direction, signal pattern 38-a~signal pattern 38-m and wiring 85-a~wiring 85-m are disposed alternately above and below the respective upper electrode groups 46. On the flexible substrate 41 in the short-axis direction, signal pattern 41-1~signal pattern 41-4, wiring 86-11~wiring 86-41, signal pattern 39-1~signal pattern 39-4 and wiring 86-12~wiring 86-42 are disposed in pairs on the left and the right side of the respective lower electrodes 48.

Upper electrode 46-a~upper electrode 46-m on the superconductor basal plate 40 of cMUT chip 20 are juxtaposed in long-axis direction X. Upper electrode 46-a~upper electrode 46-m are respectively connected to 3 rows of a plurality of transducer elements 28. Signal pattern 38-*a*~signal pattern 38-*m* of flexible substrate 42 in the vertical direction are arranged in parallel with long-axis direction X. Upper electrode 46-*a*~upper electrode 46-*m* are respectively connected to signal pattern 38-*a*~signal pattern 38-*m* on flexible basal plate 42 via wire 86 of the wire-bonding method. Also, signal pattern 38-*a*~signal pattern 38-*m* are respectively connected to wiring 85-*a*~wiring 85-*m*.

In concrete terms, upper electrode 46-*a* and signal pattern 38-*a* are connected by wire 86, and signal pattern 38-*a* is to be pulled out from wiring 85-*a* of the upper side. Also, upper electrode 46-*b* and signal pattern 38-*b* are connected, and signal pattern 38-*b* is to be pulled out from wiring 85-*b* of the lower side. In other words, upper electrode 46-N (N: a, c, e . . . ) and signal pattern 38-N are connected, and signal pattern 38-N is to be pulled out of wiring 85-N (N:a, c, e . . . ) of the upper side. Also, upper electrode 46-L (L:b, d, f . . . ) and signal pattern 38-L are connected, and signal pattern 38-L is to be pulled out of wiring 85-L (L:b, d, f . . . ) of the lower side.

In this way, by pulling out signal pattern 38-*a*~signal pattern 38-*m* and wiring 85-*a*~wiring 85-*m* alternately from the upper side and the lower side, it is possible to widen the distance between, for example, signal pattern 38-*a* and signal pattern 38-*c*, wiring 85-*a* and wiring 85-*c*. As a result, cross talk generated between the adjacent respective signal patterns 38 and wirings 85 can be reduced.

Lower electrode 48-1~lower electrode 48-4 on super-conductor basal plate 40 of cMUT 20 are juxtaposed in short-axis direction Y. Lower electrode 48-1~lower electrode 48-4 are respectively connected to signal pattern 41-1~signal pattern 41-4 and signal pattern 39-1~signal pattern 39-4 via wire 86 of the wire-bonding method. Signal pattern 41-1~signal pattern 41-4 are respectively connected to wiring 86-11~wiring 86-41. Also, signal pattern 39-1~signal pattern 39-4 are respectively connected to wiring 86-12~wiring 86-42.

In concrete terms, signal pattern 41-1~signal pattern 41-4 are disposed on the left side of lower electrode 48-1~lower electrode 48-4, and signal pattern 39-1~signal pattern 39-4 are disposed on the right side of lower electrode 48-1 lower electrode 48-4. Then lower electrode 48-1 is connected to signal pattern 41-1 and signal pattern 39-1 from the left and the right sides thereof via wire 86. The lower electrode 48-2 is connected by signal pattern 41-2 and signal pattern 39-2 from the right and the left sides thereof via wire 86. In this manner, lower electrode 48-*x* (x: whole number) is connected by signal pattern 41-*x* and signal pattern 39-*x* from the right and the left sides thereof via wire 86.

Here, since the voltage to be provided to lower electrode 48-*x* from signal pattern 41-*x* and signal pattern 39-*x* are the same, signal pattern 41-*x* and signal pattern 39-*x* are equipotential. By the respective lower electrodes 48-*x* being connected from both sides by signal pattern 41-*x* and signal pattern 42-*x* that are equipotential, the influence of parasitic impedance generated in lower electrode 48 can be reduced.

Figure 5:
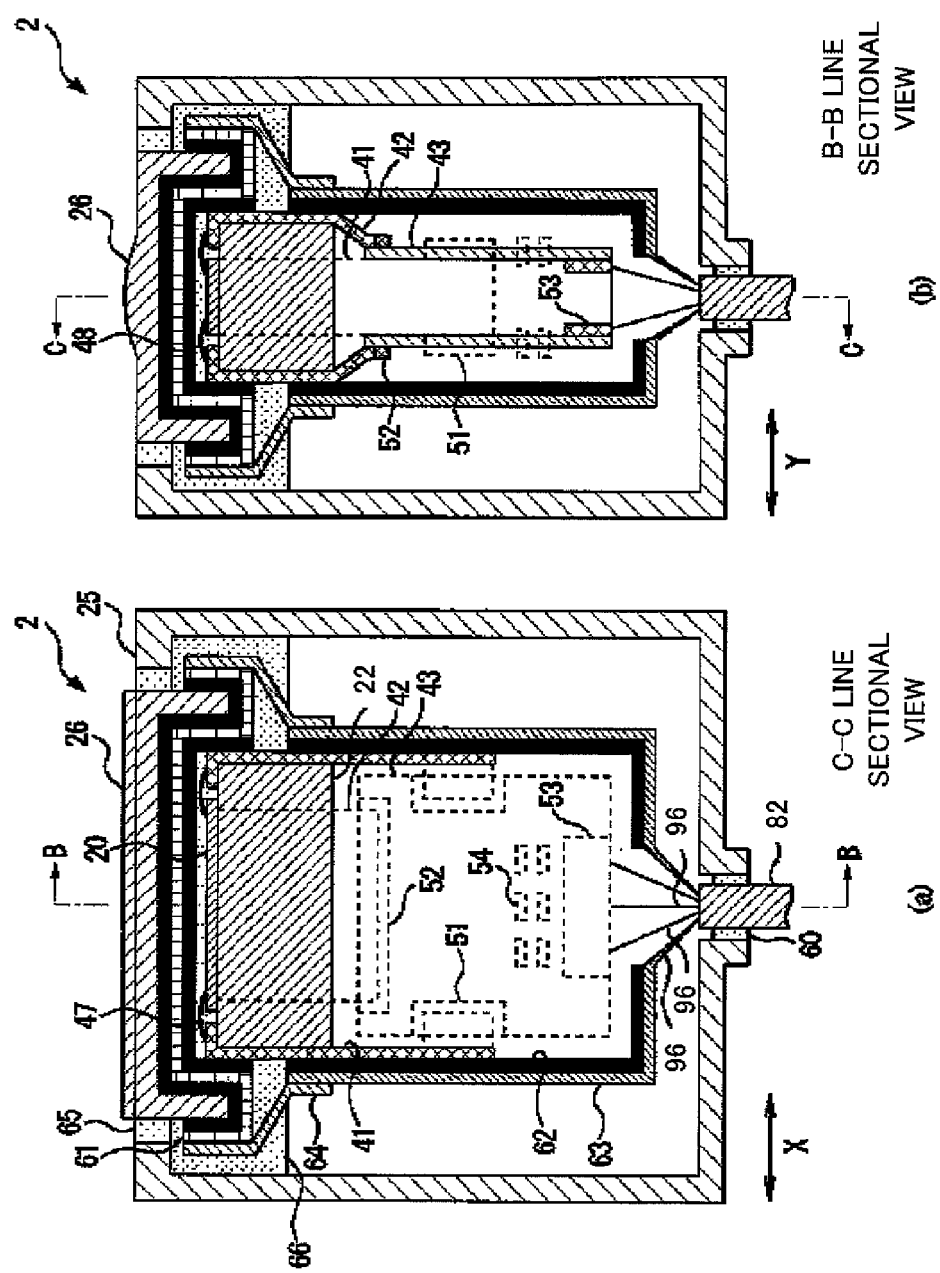
FIG. 5 illustrates the internal configuration of the ultrasonic probe related to the present invention.

FIG. 5 is a cross-sectional view of ultrasonic probe 2. FIG. 5(*a*) is a cross-sectional view in long-axis direction X of the probe. FIG. 5(*b*) is a cross-sectional view in short-axis direction Y of the probe. FIG. 5(*a*) is a C-C line cross-sectional view, and FIG. 5(*b*) is a B-B line cross-sectional view of FIG. 5(*a*).

Ultrasonic probe 2 is connected to ultrasonic diagnostic apparatus 1 via cable 82. On the ultrasonic wave transmission side of cMUT chip 20, acoustic lens 26 is provided. As for the material of acoustic lens 26, for example, silicon rubber is used. On the back surface side of cMUT chip 20, backing layer 22 is to be adhered. Along the peripheral border of the upper surface and the side surfaces in four directions of backing layer 22, flexible substrate 81 and flexible substrate 42 are provided. Flexible substrate 41 and flexible substrate 42 are adhered to the peripheral border of the upper surface of backing layer 22 in the short-axis direction and the long-axis direction respectively.

Flexible substrate 41 and flexible substrate 42 are connected to mounting base 43 via connector 51 and connector 52 respectively. To mounting base 43, a conduction circuit is provided between cable 82 and the respective terminals of flexible substrate 41 and flexible substrate 42. Also, electric component 54 such as a resistor or condenser is mounted to mounting base 43.

Wiring 86-11~wiring 86-41 and wiring 86-12~wiring 86-42 from flexible substrate 41 are connected to an inner conductor of coaxial cable 96 via connector 43 of mounting base 43. Wiring 85-*a*~wiring 85-*m* from flexible substrate 42 are connected to an inner conductor of coaxial cable 96 via connector 53 of mounting base 43.

Along the inner surface and the outer surface of acoustic lens 26, conducting layer 61 is formed. Conducting layer 61 is a Cu film formed by, for example, vapor deposition. An insulating layer may be formed along with conducting layer 61. Also, two layers of insulating layers may be formed placing conducting layer 61 therebetween.

Insulating member 62 and conductive member 63 are provided along the surface of flexible substrate 41 and flexible substrate 42. Insulating member 62 is a member having insulating property, and is a insulating tape made of, for example, silicon oxide or paraxylene. Conductive member 63 is a member having conducting property, which is, for example, a Cu tape.

Conducting layer 61 and conductive member 63 are connected via conductive member 64. Conductive member 64 is a highly dependable and highly rigid member which is more durable compared to conducting layer 61. Conductive member 64 is, for example, a Cu tape. Conductive member 64 is to be fixed to conductive member 63 provided on conductive layer 61 on the outer surface of acoustic lens 26, or the surface of flexible substrate 41 or flexible substrate 42.

Conducting member 63 is connected to an outer conductor of coaxial cable 96. Coaxial cable 96 is connected to ultrasonic diagnostic apparatus 1 being converged by cable 82.

Case 25 is provided to the sides in four directions of ultrasonic probe 2, and is fixed to the sides thereof of acoustic lens 26. An operator is to operate ultrasonic probe 2 by grasping case 25. In the gap between case 25 and acoustic lens 26, sealant 65 is filled. In the gap between case 25 and cable 82, sealant 60 is filled. Also, the gap between acoustic lens 26 and case 25 is filled by filler 66.

Figure 6:
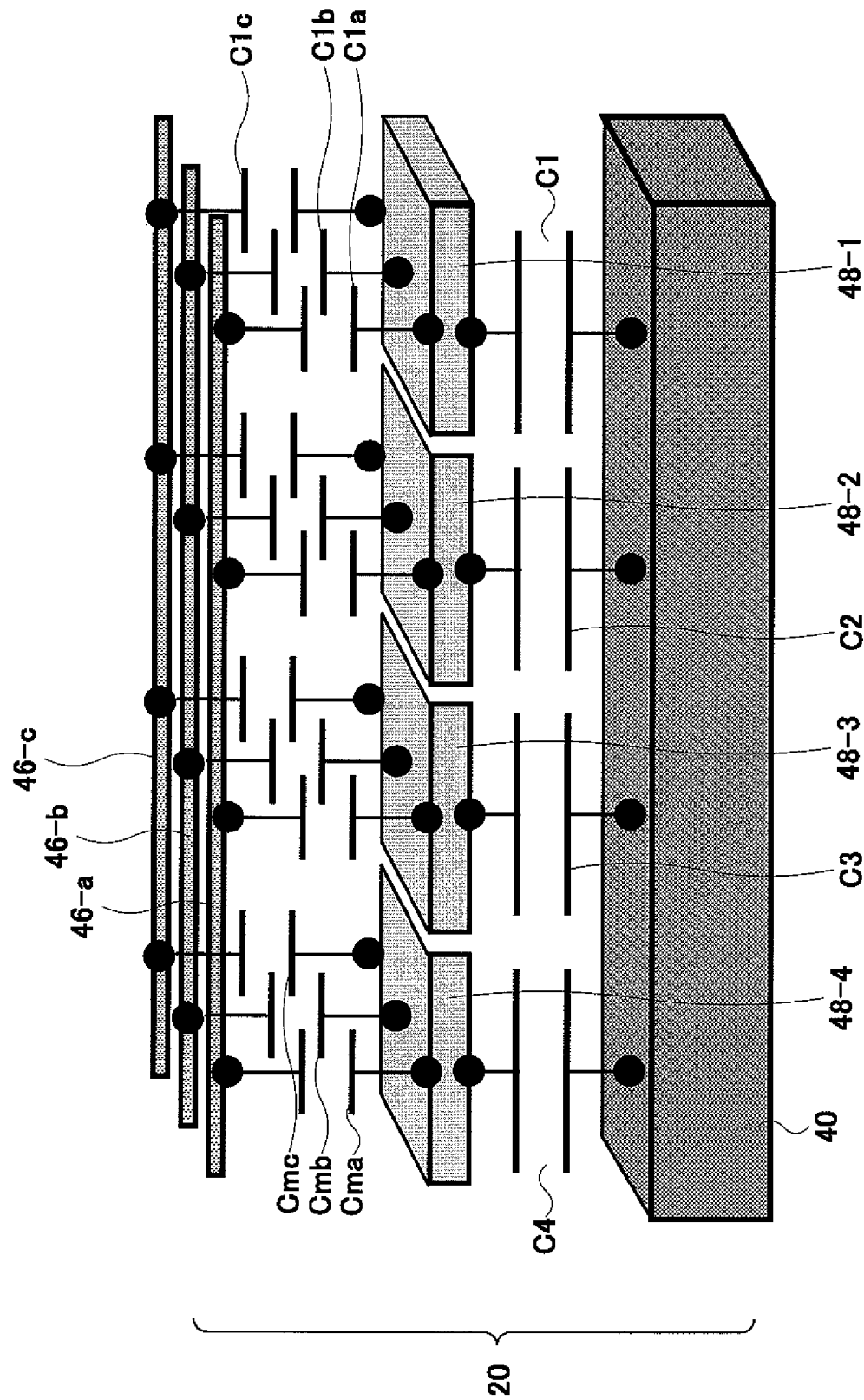
FIG. 6 illustrates the mechanism capable of reducing the influence of parasitic impedance related to the present invention.

Here, the mechanism capable of reducing the influence of parasitic impedance generated in lower electrode 48 will be described using FIG. 6 and FIG. 7. FIG. 6 shows distribution of capacitance C1*a*~capacitance Cmc between cMUT cells 20 wedged between upper electrode 46 and lower electrode 48 and distribution of capacitance C1~capacitance C4 produced in lower electrode 48-1~lower electrode 48-4 and semiconductor substrate 40. Though the number of upper electrodes is set as three and the number of lower electrodes is set as four in the present embodiment to simplify the description, the number of electrodes may be modified.

Lower electrode 48-1~lower electrode 48-4 are to be disposed orthogonal to upper electrode 46-*a*~upper electrode 46-*c*. The capacitance among cMUt cells 20 wedged between lower electrode 48-1 and upper electrode 46-*a*~upper electrode 46-*c* is set as C1*a*, C1*b* and C1*c*. In the same manner, the capacitance among cMUT cells 20 being wedged between lower electrode 48-*x* and upper electrode 46-*a*~upper electrode 46-c are set as Cma, Crab and Cmc. Also, the capacitance between lower electrode 48-1 and semiconductor substrate 40 is set as C1. In the same manner, the capacitance between lower electrode 48-2~lower electrode 48-4 and semiconductor substrate 40 is set as C2~C4.

Figure 7:
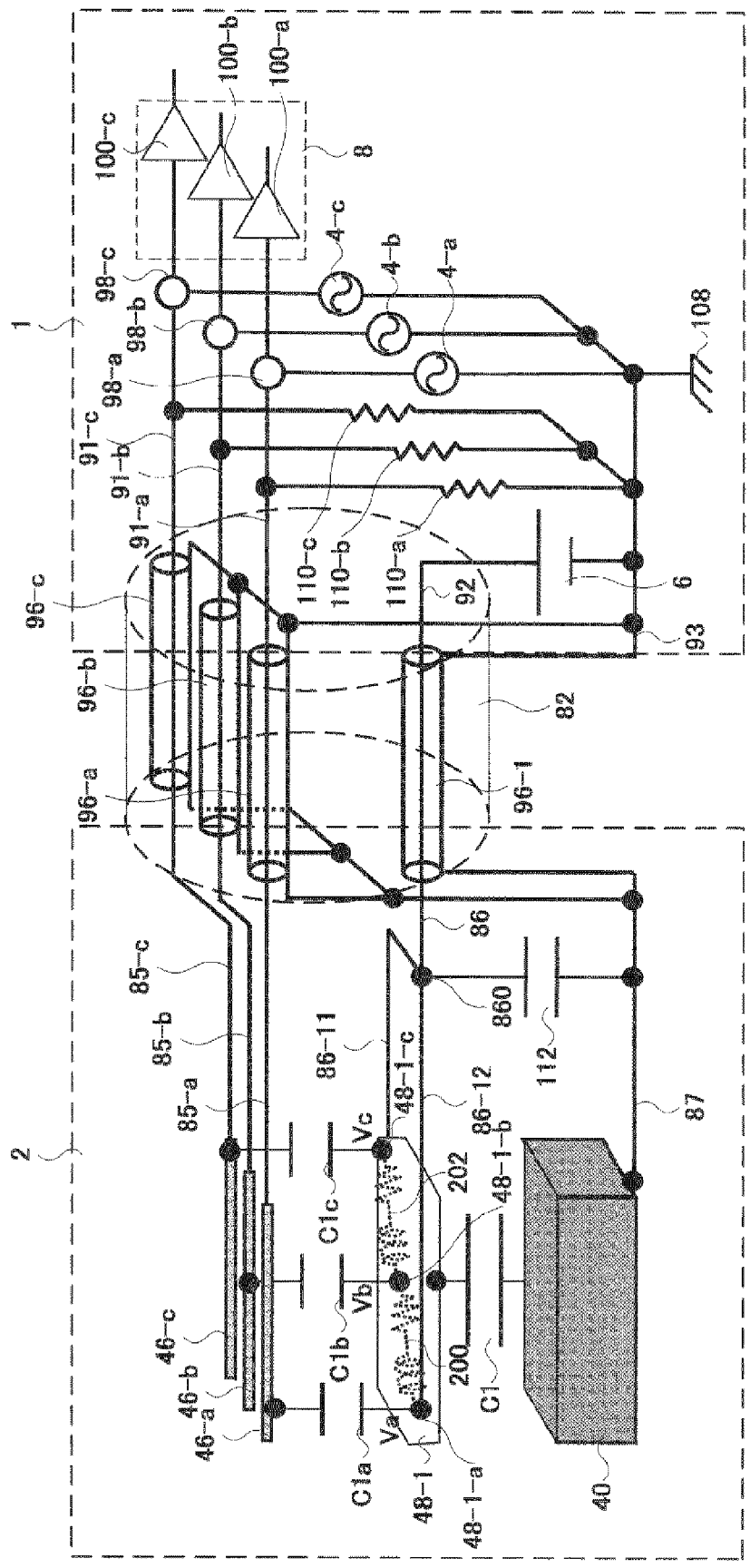
FIG. 7 illustrates the mechanism capable of reducing the influence of parasitic impedance related to the present invention.

FIG. 7 illustrates the relation of connection between ultrasonic diagnostic apparatus 1 and ultrasonic probe 2, and the pattern that two wirings are pulled out from both ends of semiconductor substrate 40. Ultrasonic diagnostic apparatus 1 and ultrasonic probe 2 are connected via cable 82. Cable 82 has a plurality of coaxial cables 96.

Upper electrode 46-a~upper electrode 46-c of transducer element are connected to wiring 85-a~wiring 85-c respectively. Wiring 85-a~wiring 85-c are connected to wiring 91-a~wiring 91-c in ultrasonic diagnostic apparatus 1 via the inner conductor of coaxial cable 96-a~coaxial cable 96-c. Wiring 91-a~wiring 91-c are connected to receiving amplifier 100-a~receiving amplifier 100-c in reception means 8 and transmission means 4-a~transmission means 4-c via transmission/reception separating circuit 98-a~transmission/reception separating circuit 98-c respectively.

Also, wiring 91-a~wiring 91-c are connected to pulldown resistor 110-a~pulldown resistor 110-c, then to ground 108. Pulldown resistor 110-a~pulldown resistor 110-c are the resistor elements for regulating the DC potential of upper electrode 46-a~upper electrode 46-c to the ground potential.

Also, wiring 86-11 and wiring 86-12 pulled out from both ends of lower electrode 48-1 are joined to terminal 860. One end outputted from terminal 860 is connected to ground 108 via by-pass condenser 112. By-pass condenser 112 is a capacitive element for signal current, for by-passing the current from lower electrode 48-1 when AC current flows from upper electrode 46-a~upper electrode 46-c to lower electrode 48-1.

The other end outputted from terminal 860 is pulled out from wiring 86, and connected to wiring 92 in ultrasonic diagnostic apparatus 1 via the inner conductor of coaxial cable 96-1. Bias means 6 is disposed between wiring 92 and wiring 93. Bias means 6 generates potential difference between upper electrode 46-a~upper electrode 46-c and lower electrode 48-a. Also, transmission means 4 applies alternating high-frequency voltage to upper electrode 46-a~upper electrode 46-c as a drive signal. In concrete terms, upper electrode 46-a~upper electrode 46-c have the condition that DC=ground (reference potential) and AC=Vpp, and lower electrode 48-a has the condition that DC=Vdc and AC=0.

Semiconductor substrate 40 is connected to wiring 87. Wiring 87 is connected to wiring 93 in ultrasonic diagnostic apparatus 1 via the outer conductor of coaxial cable 96. Wiring 93 is connected to ground 108 via a chassis ground of ultrasonic diagnostic apparatus 1.

In the case of transmitting ultrasonic waves, DC bias voltage (Va) is applied to transducer elements 28 via upper electrode 46-a~upper electrode 46-c and lower electrode 48-1, and electrical field is generated by the bias voltage (Va). Tension is produced in film body 44 by the generated electrical field, and becomes a predetermined electromechanical coupling coefficient (Sa). When drive signals are provided from transmission means 4 to upper electrode 46-a~upper electrode 46-c, ultrasonic waves are transmitted from film body 44 based on the electromechanical coupling coefficient (Sa).

Also, when DC bias voltage (Vb) is applied to transducer elements 28 via upper electrode 46-a~upper electrode 46-c and lower electrode 48-a, electrical field is generated by the bias voltage (Vb). Tension is produced in film body 44 by the generated electrical field, and becomes a predetermined electromechanical coupling coefficient (Sb). When drive signals are provided from transmission means 4 to upper electrode 46-a~upper electrode 46-c, ultrasonic waves are transmitted from film body 44 based on the electromechanical coupling coefficient (Sb).

When ultrasonic waves are transmitted/received, since lower electrode 48-1 has finite measure, parasitic impedance including lead inductance and loss resistance components are distributed to capacitance C1a~C1c. Suppose that one lower electrode 48-1 (C1a side only) is pulled out, i.e. only wiring 86-12 is connected to lower electrode 48-1, the voltage in terminal 48-1-a~terminal 48-1-c of lower electrode 48-1 will be as the formula below. Terminal 84-1-a~terminal 48-1-c here correspond to upper electrode 46-a~upper electrode 46-c.

$$v_a = C1a \cdot i_1 \quad \{\text{Formula 1}\}$$

$$v_b = C1b \cdot i_2 + (R+L) \cdot i_2 \quad \{\text{Formula 2}\}$$

$$v_c = C1c \cdot i_3 + 2(R+L) \cdot i_3 \quad \{\text{Formula 3}\}$$

For example, when an ultrasonic wave is transmitted with transmission pulsar 4-c, the current path of an ultrasonic transmission signal is transmission pulsar 4-c, transmission/reception separating circuit 98-c, wiring 91-c, wiring 85-c, upper electrode 46-c, terminal 48-1-c, parasitic impedance 202, terminal 48-1-b, parasitic impedance 200, terminal 48-1-a, C1//wiring 86-12 (//means parallel), wiring 92 and ground 108. At this time, since the current passes through parasitic impedance 202 and parasitic impedance 200, fluctuation of voltage occurs in terminal 48-1-a~terminal 48-1-c of lower electrode 48-1.

Given this factor, in the case that two terminals are pulled out of lower electrode 48-1 (C1a side and C1c side) as shown in FIG. 4 and FIG. 7, i.e. in the case that wiring 86-12 and wiring 86-11 are connected to terminal 48-1-a and terminal 48-1-c, when an ultrasonic wave is transmitted with transmission pulsar 4-c, fluctuation of current is not generated since the current is not split into parasitic impedance 200 and parastic impedance 202.

Also, when an ultrasonic wave is transmitted with transmission pulsar 4-b, the voltage in terminal 48-1-a~terminal 48-1-c of lower electrode 48-1 turn out as the formulas below.

$$C1a \cdot i_1 \quad \{\text{Formula 4}\}$$

$$v_b = C1b \cdot i_2 + \frac{1}{2}(R+L) \cdot i_2 \quad \{\text{Formula 5}\}$$

$$v_c = C1c \cdot i_3 \quad \{\text{Formula 6}\}$$

Since the current is split into parasitic impedance 200//parasitic impedance 202, the influence of parasitic impedance is reduced to half of the case that only one terminal is pulled out of lower electrode 48-1 (C1a side only). Here, if the impedance of C1 is sufficiently smaller than the parasitic impedance when the capacitance value of C1 is compared to that of Cma, the degree of current that is split into parasitic impedance can be remarkably reduced. In this manner, the influence of parasitic impedance generated in lower electrode 48 can be reduced.

(Second Embodiment)

Figure 8:
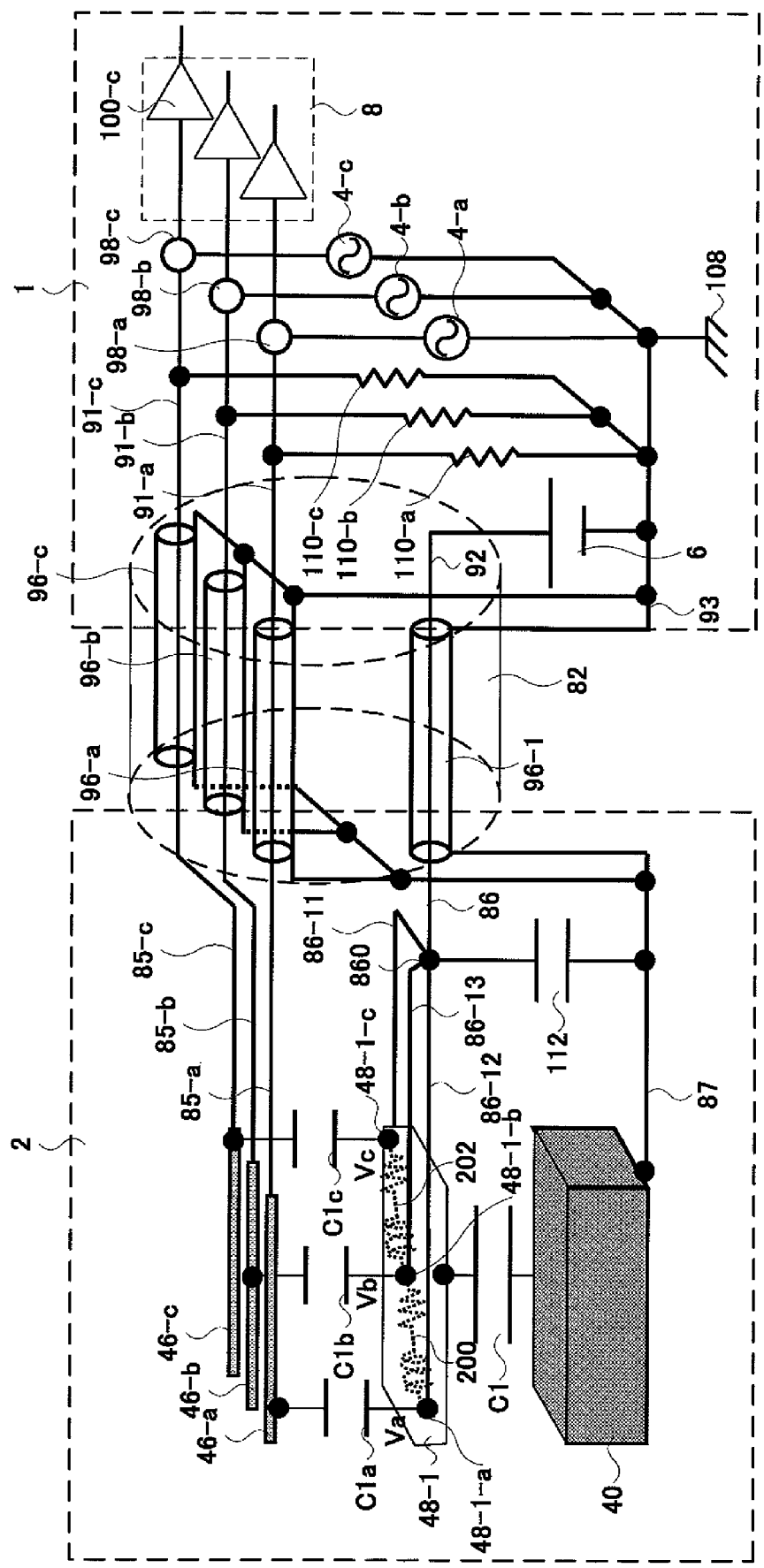
FIG. 8 illustrates second embodiment of the present invention.

Second embodiment will be described using FIG. 8. The difference from first embodiment is that three terminals are pulled out of lower electrode 48-1. As shown in FIG. 8, in the case that 3 terminals are pulled out of lower electrode 48-1 (the sides of C1a, C1b and C1c), i.e. wiring 86-12, wiring 86-13 and wiring 86-11 are respectively connected to terminal 48-1-a, terminal 48-1-b and terminal 48-1-c. When an ultrasonic wave is transmitted with transmission pulsar 4-*b*, the voltages in terminal 48-1-*a*~terminal 48-1-*c* of lower electrode 48-1 turn out as the formulas below.

$$v_a = C1a \cdot i_1 \quad \{\text{Formula 7}\}$$

$$v_b = C1b \cdot i_2 \quad \{\text{Formula 8}\}$$

$$v_c = C1c \cdot i_3 \quad \{\text{Formula 9}\}$$

Since current does not flow into parasitic impedance 200 and parasitic impedance 202, there will be no influence of parasitic impedance. In this manner, the influence of parasitic impedance generated in lower electrode 48 can be reduced.

Also, 4 or more terminals may be pulled out of lower electrode 48-1, for example, the same number of terminal 48-1-*m* and wiring 86-1*m* as the number of upper electrodes may be provided. By pulling a plural number of terminals out of lower electrode 48-1, the influence of parasitic impedance generated in lower electrode 48 can be reduced.

(Third Embodiment)

Third embodiment will be described below. The difference from the first and second embodiments is that the cross-section area which is orthogonal to the long-axis direction of lower electrode 48 or the length in the long-axis direction of lower electrode 48 is changed.

For example, by increasing the thickness of lower electrode 48 from 100 nm to 200 nm, the cross-section area orthogonal to the long-axis direction of lower electrode 48 becomes double. Therefore, by doubling the cross section area which is orthogonal to the long-axis direction of lower electrode 48, it is possible to reduce parasitic impedance 200 and parasitic impedance 202 by half, whereby reducing the influence of parasitic impedance 200 and parasitic impedance 202 by half.

Figure 9:
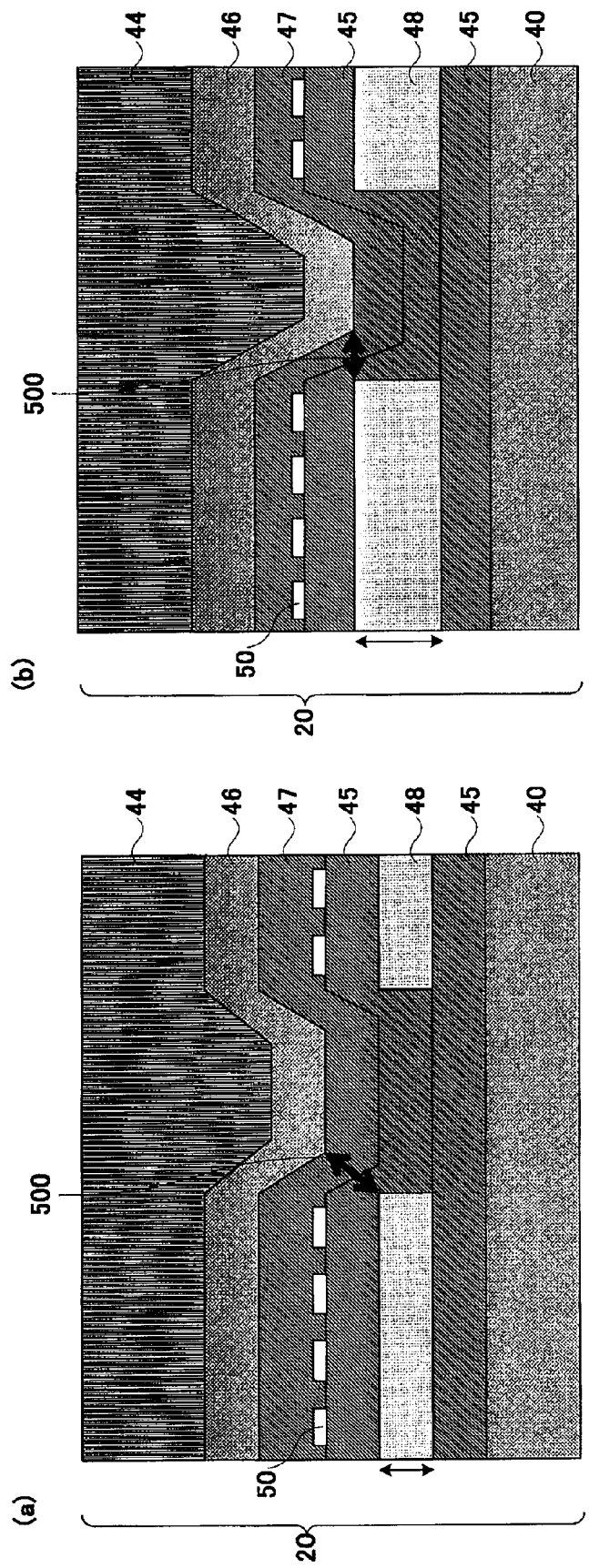
FIG. 9 illustrates third embodiment of the present invention.

Thickness restriction of lower electrode 48 will be described below referring to FIG. 9. Lower electrode 48 shown in FIG. 9(*a*) is the standard thickness, and lower electrode 48 shown in FIG. 9(*b*) shows the condition that the thickness thereof is increased by more than double of the thickness shown in FIG. 9(*a*). In FIG. 9(*b*), the thickness of lower electrode 48 is thicker than the sum of the thickness of film body 45 and the thickness of frame body 47. Therefore, the bump of upper electrode 46 becomes larger, and the portion where electrical charge tends to be converged such as the corner of upper electrode 46 gets closer to lower electrode 48. When they are too close, even electric field intensity being smaller than the withstand voltage of frame body 47 becomes the factor for generation of dielectric breakdown. Thus the thickness of lower electrode 48 is designated so that the portion where electric charge tends to be converged such as the corner of upper electrode 46 does not get too close to lower electrode 48. For example, the thickness of lower electrode 48 is designated so that the length 500 between upper electrode 46 and lower electrode 48 becomes longer than 250 nm.

Also, for example, by changing the length of lower electrode 48 (long-axis direction (X-axis direction)) from 50 mm to 25 mm, the length of lower electrode 48 is reduced by half. In this manner, by reducing the length of lower electrode 48 by half, it is possible to reduce parasitic impedance 200 and parasitic impedance 202 by half. Both ends of lower electrode 48 related to the present embodiment are slightly protruded from the position where a plurality of transducer elements 28 are disposed, so as to shorten the length in the long-axis direction of lower electrode 48. Though these protruded portions have sufficient width for implementing wire bonding of wiring 86, they are set so that the length of lower electrode 48 in the long-axis direction becomes as short as possible. For example, the width of both ends of protruded portions should be about 200 µm~1.5 mm.

As described above, parasitic impedance of lower electrode 48 is in reverse proportion to the cross-section area of lower electrode 48, and is in reverse proportion to the length of lower electrode 48. Parasitic impedance of lower electrode 48 can be reduced using such characteristics.

(Fourth Embodiment)

Figure 10:
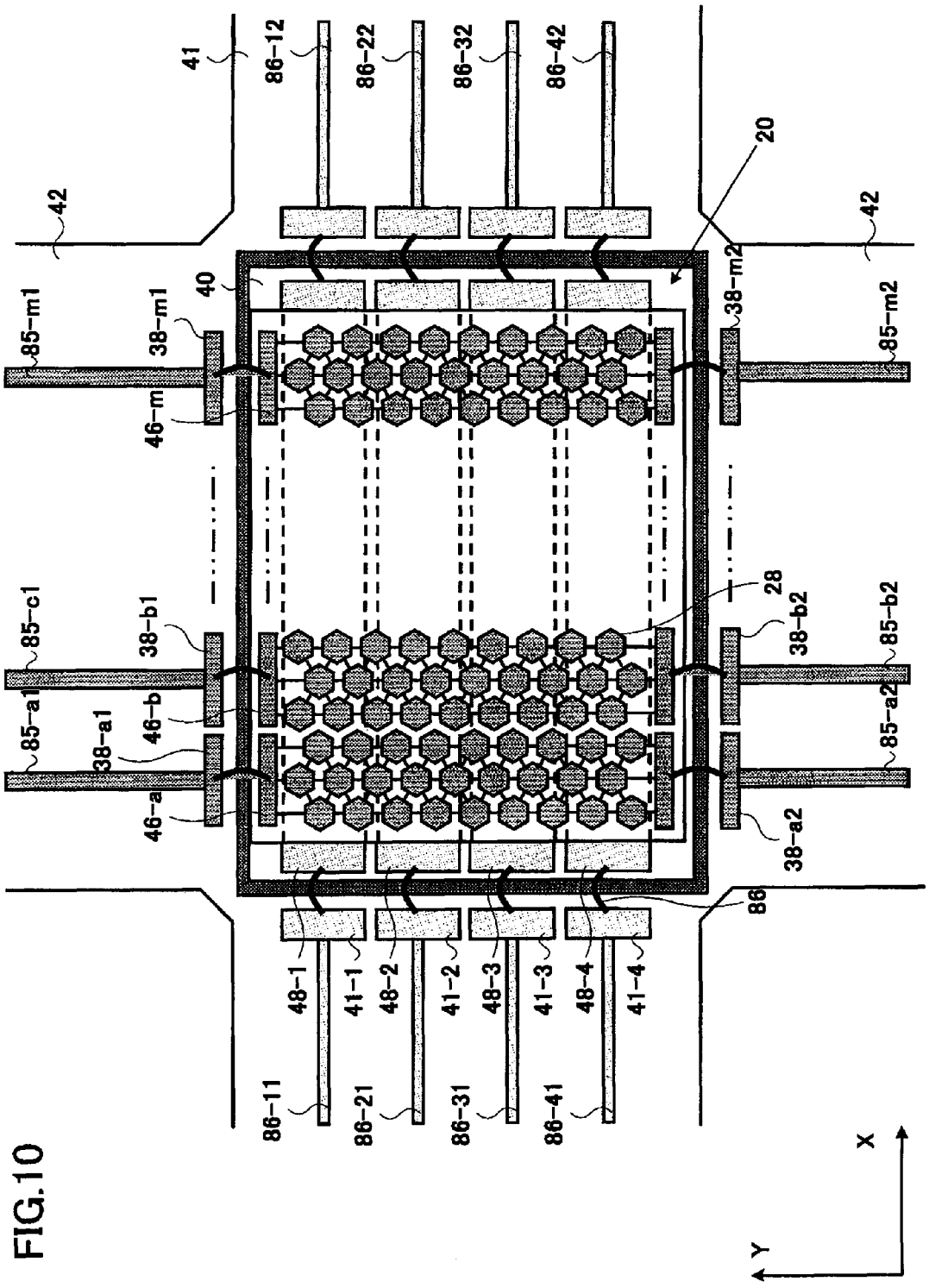
FIG. 10 illustrates fourth embodiment of the present invention.

Fourth embodiment will be described referring to FIG. 10. The difference from first embodiment~third embodiment is that the upper electrode 46 is pulled out from vertical directions.

Upper electrode 46-*a*~upper electrode 46-*m* on semiconductor basal plate 40 of cMUT chip 20 are juxtaposed in long-axis direction X. Upper electrode 46-*a*-upper electrode 46-*m* are respectively connected to signal pattern 38-*a*1~signal pattern 38-*m*2 and signal pattern 38-*a*2~signal pattern 38-*m*2 via wiring 86 of the wire bonding method. Signal pattern 38-*a*1~signal pattern 38-*m*1 are connected to wiring 85-*a*1~wiring 85-*m*1 respectively. Also, signal pattern 38-*a*2~signal pattern 38-*m*2 are connected to wiring 85-*a*2~wiring 85-*m*2 respectively.

In concrete terms, signal pattern 38-*a*1~signal pattern 38-*m*1 are disposed on the upper side of upper electrode 46-*a*~upper electrode 46-*m*, and signal pattern 38-*a*2~signal pattern 38-*m*2 are disposed on the lower side of upper electrode 46-*a*~upper electrode 46-*m*. Then upper electrode 46-*a* is connected to signal pattern 38-*a*1 and signal pattern 38-*a*2 from both sides of the vertical direction. Upper electrode 46-*b* is connected to signal pattern 38-*b*1 and signal pattern 38-*b*2 from the vertical direction. Upper electrode 46-*m* is connected to signal pattern 38-*m*1 and signal pattern 38-*m*2 from the vertical direction.

As stated above, by pulling out upper electrode 46 from the vertical direction, the influence of the parasitic impedance generated in upper electrode 46 can be reduced. Since the mechanism of reducing parasitic impedance is the same as the case of lower electrode 48 described in the first embodiment, the explanation thereof will be omitted.

The invention claimed is:

1. An ultrasonic diagnostic apparatus comprising:
    an ultrasonic probe configured to transmit/receive ultrasonic waves with a plurality of transducers to/from an object to be examined;
    a transmission unit configured to provide a drive signal to the plurality of transducers;
    a bias unit configured to supply a bias voltage to the plurality of transducers;
    a reception unit configured to convert the received ultrasonic waves from the object into received reflected echo signals;
    a computer having at least one processor pre-configured to operate as:
        a phasing adding unit configured to perform a phasing and adding process on the received reflected echo signals;
        an image processing unit configured to construct an ultrasonic image based on outputted signals from the phasing adding unit; and
        a display unit configured to display the ultrasonic image from the image processing unit;
    an operation unit including input hardware, configured to receive commands to the computer, via input by an operator,
    wherein the ultrasonic probe is a capacitive micromachined ultrasonic transducer (cMUT) chip, the cMUT chip including: a plurality of upper electrodes, a plurality of lower electrodes, and a wiring arrangement connected to supply the bias voltage from the bias unit to the plurality of upper electrodes and the plurality of lower electrodes, and the wiring arrangement is connected at two or more places of at least one upper electrode of the plurality of upper electrodes and at two or more places of at least one lower electrode of the plurality of lower electrodes, so as to apply the bias voltage to reduce cross talk by reducing parasitic impedance generated by the plurality of upper electrodes or the plurality of lower electrodes.

2. The ultrasonic diagnostic apparatus according to claim 1,
wherein both ends of the at least one lower electrode are respectively connected to the wiring arrangement.

3. The ultrasonic diagnostic apparatus according to claim 2,
wherein the both ends of the lower electrode are portions protruded from disposal positions of transducer elements provided on the lower electrode.

4. The ultrasonic diagnostic apparatus according to claim 3,
wherein width of each protruded portion of the portions protruded, is in a range from 200 micrometer to 1.5 millimeter.

5. The ultrasonic diagnostic apparatus according to claim 1,
wherein respective wirings of the wiring arrangement, which are connected to the two or more places of the at least one lower electrode, have equipotential applied thereto by the bias voltage.

6. The ultrasonic diagnostic apparatus according to claim 1,
wherein a cross-section area which is orthogonal to a long-axis direction of the at least one lower electrode, is set so that a spacing between the at least one upper electrode and the at least one lower electrode is greater than a predetermined interval.

7. The ultrasonic diagnostic apparatus according to claim 6,
wherein the spacing between the at least one upper electrode and the at least one lower electrode, is greater than 250 nm.

8. The ultrasonic diagnostic apparatus according to claim 1,
wherein ends of the plurality of upper electrodes are respectively connected to the wiring arrangement, in opposing directions for adjacent upper electrodes.

9. An ultrasonic probe comprising:
a capacitive micromachined ultrasonic transducer (cMUT) chip;
wherein the cMUT chip including a plurality of upper electrodes, a plurality of lower electrodes, and a wiring arrangement connected to supply a bias voltage to the plurality of upper electrodes and the plurality of lower electrodes and the wiring arrangement is connected at two or more places of at least one upper electrode of the plurality of upper electrodes and at two or more places of at least one lower electrode of the plurality of lower electrodes, so as to apply the bias voltage to reduce cross talk by reducing parasitic impedance generated by the plurality of upper electrodes or the plurality of lower electrodes.

\* \* \* \* \*